United States Patent [19]

Bossle et al.

[11] Patent Number: 4,565,787

[45] Date of Patent: Jan. 21, 1986

[54] HIGH PERFORMANCE LIQUID CHROMATOGRAPHY (HPLC) ANALYSIS OF SULFUR MUSTARDS AND THEIR DECOMPOSITION BY-PRODUCTS BY DERIVATIZATION

[75] Inventors: Paul C. Bossle, Baltimore; John J. Martin, Joppa; Emory W. Sarver; Harold Z. Sommer, both of Havre de Grace, all of Md.

[73] Assignee: The United States of America as represented by the Secretary of the Army, Washington, D.C.

[21] Appl. No.: 492,862

[22] Filed: May 9, 1983

[51] Int. Cl.$^4$ ..................... G01N 33/00; C07C 143/78
[52] U.S. Cl. ........................................ 436/120; 564/91
[58] Field of Search ........................... 564/91; 436/120

[56] References Cited

U.S. PATENT DOCUMENTS 3,107,229  10/1963  Malz et al. ........................ 564/91 X
3,542,865  11/1970  Bayer ................................... 564/91
4,085,093  4/1978  Hopper ............................. 564/91 X Primary Examiner—Paul F. Shaver
Attorney, Agent, or Firm—Anthony T. Lane; Robert P. Gibson; Edward F. Costigan

[57] ABSTRACT

A method for the simultaneous detection, separation and analysis by reverse phase HPLC of sulfur mustard type compounds and their major hydrolysis and oxidation by-products utilizes a novel precolumn enhancement derivatization procedure. The method involves the reaction of these nonchromophoric sulfides with N-halogeno-N-metal arylsulfonamidates on a microscale to produce UV or visible absorbing or fluorescing arylsulfonylsulfilimine compounds. These arylsulfonylsulfilimine derivatives can then be readily separated on a low polarity C-18 column by reverse phase HPLC. The method permits quantitation of these sulfides by UV detector response in quantities as small as 20 nanograms.

10 Claims, 2 Drawing Figures

HIGH PERFORMANCE LIQUID CHROMATOGRAPHY (HPLC) ANALYSIS OF SULFUR MUSTARDS AND THEIR DECOMPOSITION BY-PRODUCTS BY DERIVATIZATION

GOVERNMENTAL INTEREST

The invention described herein may be manufactured, used and licensed by or for the Government for Governmental purposes without payment to us of any royalties thereon.

BACKGROUND OF THE INVENTION

There is a need to be able to readily detect, separate and quantify trace amounts of sulfur mustard agents and their decomposition by-products in aqueous solution in combat situations for detecting agent use as well as in the laboratory for analyzing intelligence samples. The decomposition by-products are more likely to be encountered in the environment rather than the agent alone. This need is also present in environmental studies and generally in analytical methodology for the identification of alkyl sulfides in an aqueous matrix.

Sulfur mustards are currently analyzed by colorimetry using 4-(p-nitrobenzyl)pyridine (DB-3) (Holzman, G. Jr. Swift, E. H. and Niemann, C. OSRD 4288, The Colorimetric Estimation of NH-3 and DB-3, 27 Oct. 1944; Esptein, J. Rosenthal, R. W. and Ess, R. J. Uses of 4-(p-Nitrobenzyl)pyridine As Analytical Reagent for Ethyleneimines and Alkylating Agents, *Anal. Chem.* 27, 1435-9 (1955). This is a general test which gives positive results for practically all alkylating agents and false positives for some acylating agents. However, this test is not effective for the decomposition by-products of sulfur mustards.

Gas chromatography (GC) has also been employed for analyzing some mustards (Fisher, T. L., Jaskot, M. and Sass, S. Edgewood Arsenal Technical Report 4321, Trace Estimation and Differentiation of Some Mustards Employing Gas-Liquid Chromatography). However, aqueous samples cannot be analyzed directly by GC but must undergo a lengthy extraction and workup procedure before analysis can be performed.

High performance (pressure) liquid chromatography (HPLC) using a reverse phase column has achieved state-of-art analytical separation technology due to the development of improved columns and more sensitive detectors. The most commonly used sensitive detector is based on ultraviolet/visible absorption or fluorescence. However, sulfur mustards and their decomposition by-products do not absorb or fluoresce in this spectral region and hence as such are not amenable to HPLC analysis with a UV or fluorescent detector.

SUMMARY OF THE INVENTION

In accordance with the present invention there is provided a method for the simultaneous detection, separation and analysis of sulfur mustards and their major hydrolysis and oxidation by-products, as well as of mixtures of non-chromophoric aliphatic sulfides generally. The method comprises reacting a mixture of aliphatic sulfides of the formula $R^1$—S—$R^2$, wherein $R^1$ and $R^2$ are alkyl radicals which may or may not contain substituents and may be the same or different, with an alkali metal arylsulfochloramide of the formula aryl-$SO_2$NMe Cl, wherein Me is an alkali metal, to produce a mixture of corresponding ultraviolet fluorescent arylsulfonylsulfilimine compounds according to the equation:

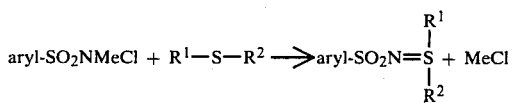

wherein Me, $R^1$ and $R^2$ have the meanings defined above, separating the mixture into the individual arylsulfonylsulfilimine compounds by reverse phase high pressure liquid chromatography, and fluorescing the individual arylsulfonylsulfilimine compounds by ultraviolet radiation. The invention is particularly valuable for the analysis of mixtures of sulfur mustard type compounds and their decomposition by-products of the formula $R^1$—S—$R^2$, wherein $R^1$ is 2-chlorethyl, 2-hydroxyethyl, or vinyl, and $R^2$ is 2-chloroethyl, 2-hydroxyethyl, vinyl or an unsubstituted alkyl group of 1 to 6 carbon atoms.

The reaction of alkylsulfides with salts of N-chloroarylsulfonamides, such as chloramine-B or -T, in aqueous solution has been widely employed as a facile means of preparing crystalline and innocuous derivatives of alkyl sulfides for characterization purposes. The present invention utilizes this reaction on a microscale to convert alkyl sulfides, which do not fluoresce in the UV region, into UV absorbing arylsulfonylsulfilimines, which when dissolved in a suitable solvent, such as aqueous methanol or ethanol and aqueous acetonitrile, can then be readily separated by reverse phase HPLC and quantified by UV detector response. Analysis is made by comparison with standard solutions of known arylsulfonylsulfilimine derivatives of alkylsulfides.

In HPLC the chromatographic stationary phase is relatively nonpolar while the solvent or mobile phase is relatively polar. This derivatization technique is also useful in that sample polarity is reduced, thus improving subsequent column separation. In this manner these sulfides can be quantified by photometric or fluorometric detector response in amounts as low as 20 nanograms.

DETAILED DESCRIPTION OF THE INVENTION

Figure 1:
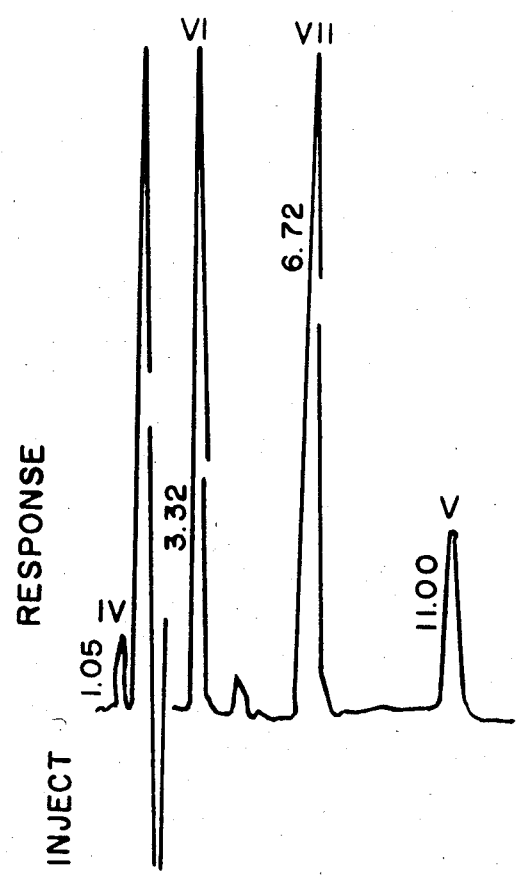

The invention is particularly valuable for the reverse phase HPLC separation and analysis of mixtures of sulfur mustards and major hydrolysis and oxidation by-products thereof. In the following description a model sulfur mustard, 2-chloroethyl ethylsulfide (I), and its major decomposition by-products, 2-hydroxyethyl ethyl sulfide (II) and vinyl ethylsulfide (III)

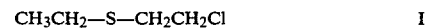 I

 II

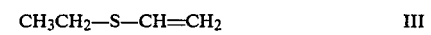 III are reacted with sodium benzenesulfochloramide (chloramine B) (IV), which contains a strong ultraviolet chromophore, on a microscale in aqueous alcoholic medium to form novel ultraviolet absorbing phenylsulfonylsulfilimines according to the following equation:

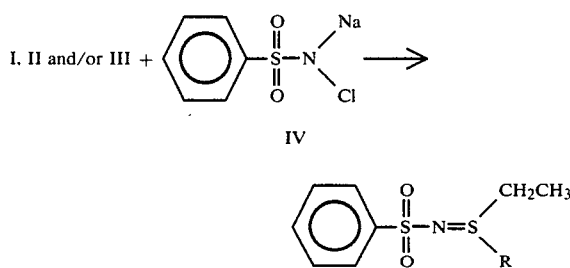

wherein

R is ClCH$_2$CH$_2$—=I→V
HOCH$_2$CH$_2$—=II→VI
is CH$_2$=CH$_2$—=III→VII

Compounds V, VI and VII are then separated by HPLC and quantified by UV detector response, as described below:

MATERIALS

Instrumentation

HPLC analyses were carried out using a Waters Associates High Pressure Liquid Chromatograph consisting of two Model 6000A Pumps, a U6K Injector, a Model 440 UV Detector, a 730A Data Module, and a 720A Systems Controller. Separation was carried out using a Waters Associates Radial-PAK C18 (10μ) Column.

Infrared spectra were recorded on a Perkin-Elmer 283-B Spectrophotometer. $^1$H NMR spectra were recorded using a Varian A-60-D Spectrometer. GC-MS analysis was carried out using a Hewlett-Packard 5985A equipped with a 10 m×0.25 mm ID glass, WCOT, SP2100 column.

Chemicals

Water used for HPLC was distilled and deionized (10-14 megohm-cm). Acetonitrile and methanol were HPLC grade (Burdick and Jackson, Muskegon, MI, USA). Compounds I and III were obtained from Fairfield Chemical Co., Inc. (Blythewood, SC, USA). Compound II was obtained from Aldrich Chemical Co., Inc. (Milwaukee, WI, USA). Compound IV was obtained from Eastman Kodak (Rochester, NY, USA) and purified. All chemicals used gave analytical data consistent with their chemical structure.

METHODS

Preparation of the V, VI and VII Standards for HPLC

Quantities of each of the three sulfilimines were prepared for use as standards to determine optimum chromatographic conditions and effectiveness of analytical derivatization. The sulfide (1.0 m mole) and IV (1.1 m mole) were stirred together in 10 ml of 30% cold aqueous methanol for one hour. a white crystalling precipitate appeared almost immediately in all cases. The precipitate was filtered off, washed with a small quantity of water, dried, and washed with ether. The precipitate was then recrystallized from ethanol. Spectral data were in agreement with the assigned structures.

S-Ethyl-S-chloroethyl-N-phenylsulfonylsulfilimine (V)

The recrystallized product was obtained by the general procedure outlined above: yield 89%; m.p. 109°-110° C. (Found: C, 42.9; H, 5.1; Cl, 12.8; N, 5.1; S, 22.9. Calc. for C$_{10}$H$_{14}$ClNS$_2$O$_2$: C, 42.9, H, 5.0; Cl, 12.7; N, 5.0; S, 22.9).

S-Ethyl-S-2-hydroxyethyl-N-phenylsulfonylsulfilimine (VI)

The recrystallized product was obtained by the general procedure outlined above except that water alone was used as the reaction solvent and ether: chloroform was used for recrystallization. The yield was 83%; m.p. 75°-76.5°. (Found C, 45.8; H, 5.8; N, 5.6; S, 24.5 Calc. for C$_{10}$H$_{15}$NS$_2$O$_3$: C, 45.9, H, 5.8; N, 5.4; S, 24.5).

S-Ethyl-S-vinyl-N-phenylsulfonylsulfilimine (VII)

The recrystallization product was obtained by the general procedure outlined above: yield, 82%; m.P. 85°-86°. (Found C, 49.1; H, 5.2; N, 6.0; S, 26.5. Calc. for C$_{10}$H$_{13}$NS$_2$O$_2$: C, 49.3; H, 5.4; N, 5.8; S, 26.4).

Chromatographic Procedure

Analytical separations were performed under the following conditions: sample size, 20 μl; flow rate, 1.5 ml/min; column temperature, ambient; mobile phase, 30% acetonitrile: water; UV. detector, 254 nm.

Standard solutions of V, VI and VII were injected onto the column and their retention times determined. Calibration curves conforming to Beer's law were obtained by injecting known concentrations (1.0 μg, 2.0 μg, 4.0 μg, 10.0 μg, and 20.0 μg per ml) of the sulfides as sulfilimine derivatives onto the column in triplicate and measuring the resulting peak areas.

Analytical Derivatization

To one equivalent of each of the sulfides in one ml of methanol is added two equivalents of IV. The mixture was heated with stirring at 60° C. for one hour. After cooling, 20 μl samples were introduced into the column through a continuous flow loop injector. Peak areas were measured and computed with an on-line integrator (Data Module).

In this way, concentrations of I, II, and III were prepared singly and in combined mixture at 1.0 μg, 2.0 μg, 4.0 μg, 10.0 μg, and 20.0 μg/ml for detection as the sulfilimines species.

RESULTS AND DISCUSSION

Arylsulfonylsulfilimines show a strong absorption peak around 230 nm (log E 4.0-5.0) and a weak absorption peak in the area of 270 nm (log E 3.0-4.5) Gilchrist, T. L. and Moody, L. J. The Chemistry of Sulfilimines, Chem. Rev., 77 (No. 3) 409 (1977). As seen in Table I, compounds V, VI and VII show strong absorption peaks at 224-225 nm as well as a weak absorption at 272 nm. Another weak peak was also observed for all three compounds at 265 nm. Also in Table 1, the log E values at 254 nm for V, VI and VII are shown.

TABLE 1

| | UV Spectra of V, VI and VII in Acetonitrile | | | | | |
|---|---|---|---|---|---|---|
| Compound | λ$_1$ (nm) | Log E$_1$ | λ$_2$ (nm) | Log E$_2$ | λ$_3$ (nm) | Log E$_3$ | Log E$_{254}$ |
| V | 224 | 3.9 | 265 | 2.7 | 272 | 2.6 | 2.7 |
| VI | 225 | 3.9 | 265 | 2.7 | 272 | 2.6 | 2.7 |
| VII | 226 | 4.0 | 264 | 2.8 | 272 | 2.7 | 2.9 |

The qualitative capability for this technique is illustrated in the chromatogram of FIG. 1 in which the complete separation of V,VI, and VII as well as IV is achieved in 15 minutes.

The retention times for the phenylsulfonylsulfilimine derivatives and excess chloramine-B reagent under the stated conditions are shown in Table 2. Excess chloramine-B reagent is unretained on the column and does not interfere with the analysis.

TABLE 2

Retention Times of the Phenylsulfonylsulfilimine Derivatives

| Compound | Retention Time (Min) |
|---|---|
| IV | 1.05 |
| VI | 3.32 |
| VII | 6.72 |
| V | 11.00 |

Figure 2:
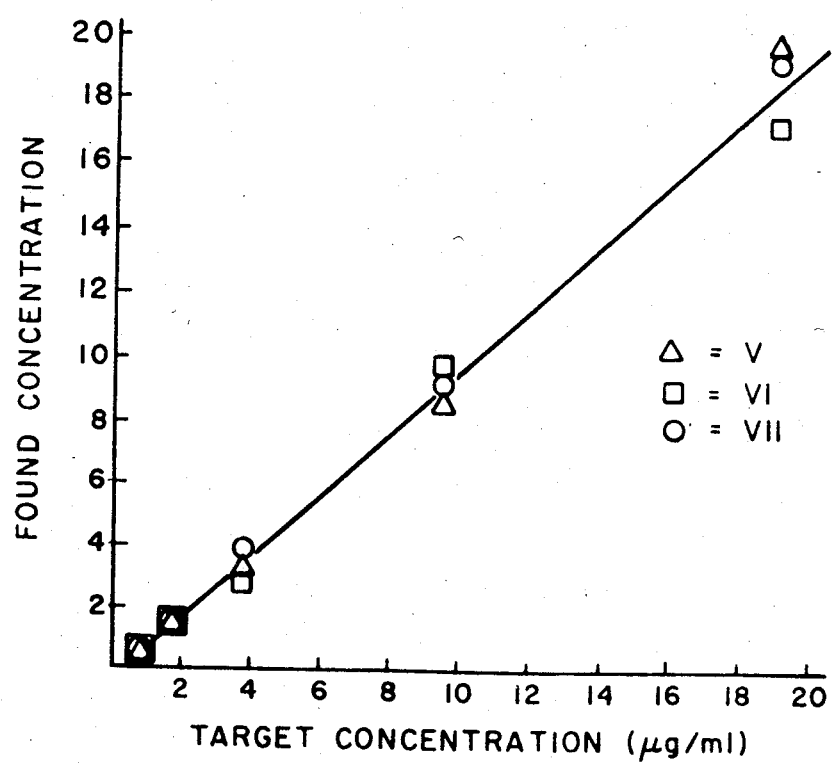

Quantitation was also readily achieved by HPLC. This is illustrated in FIG. 2. The reactions were reproducible and detector response was linear for I, II, and III in concentrations of 1.0–20.0 µg/ml. The overall efficiency of the derivatization reaction for the three sulfides was 85–99% by comparison with standardized materials. The detection limits for I, II, and III were 10, 12 and 21 nanograms, respectively. The limits of detection are based on the method described by Hubaux and Vos "Decision and Detection, Limits for Linear Calibration Curves", *Anal. Chem.* 42 (8):849 using a 95% confidence level with alpha and beta being equal to 5% (i.e. one out of 20 datum may fall outside 2 standard deviations of the fitted curve).

The method of the present invention can be similarly employed for the separation and analysis of mixtures of other sulfur mustard type compounds and their major hydrolysis and oxidation by-products as well as other aliphatic sulfides generally. Suitable sulfides include bis(2-chloroethyl)sulfide, bis(2-hydroxyethyl)sulfide, divinylsulfide, dimethylsulfide, diethylsulfide, ethyl methyl sulfide, dipropyl sulfide, ethyl propyl sulfide and ethyl n-hexyl sulfide. Also the HPLC process of the present invention can be carried out using other separatory column materials than C18. The $C_{18}$ separatory packing is made by chemically bonding a $C_{18}$ alkyl group to micro particles of fully porous silica at 10% $C_{18}$ alkyl by weight. The general chemical structure is as follows:

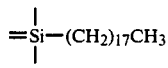

Reverse phase HPLC normally involves a relatively non-polar stationary phase (e.g. $C_{18}$ mentioned above) used in conjunction with a very polar (e.g. aqueous) mobile phase to separate a wide variety of less polar solutes.

Other separatory packing materials suitable for use in the present invention include micro particles of fully porous silica bonded to —$C_8$ alkyl, —R—CN, —R—NH$_2$, and

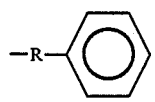

groups, wherein R is an alkylene radical.

The nature of the separatory material is not critical to the HPLC process for separation and analysis of sulfur mustards and alkylsulfides.

We claim:

1. A method for the simultaneous detection, separation, and analysis of a mixture of non-chromophoric aliphatic sulfides, which comprises:

reacting a mixture of said aliphatic sulfides of the formula $R^1$—S—$R^2$, wherein $R^1$ and $R^2$ are alkyl radicals, which may or may not contain substituents and may be the same or different, with an alkali metal arylsulfochloramide of the formula aryl-SO$_2$NMeCl, wherein Me is an alkali metal, to produce a mixture of corresponding ultraviolet fluorescent arylsulfonylsulfilimine compounds according the the following equation:

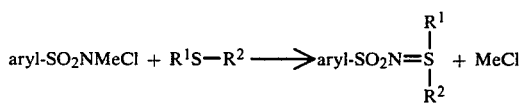

wherein Me, $R^1$ and $R^2$ have the aforesaid definitions;

separating the mixture of arylsulfonylsulfilimine compounds into the individual compounds by high pressure liquid chromatography (HPLC) and fluorescing the individual arylsulfonylsulfilimines by ultraviolet radiation.

2. A method according to claim 1, wherein the aliphatic sulfides have the formula:

$$R^1\text{—S—}R^2$$

wherein $R^1$ is 2-chloroethyl, 2-hydroxyethyl or vinyl, and $R^2$ is 2-chlorethyl, 2-hydroxyethyl, vinyl or an unsubstituted alkyl group of 1 to 6 carbon atoms, and the corresponding arylsulfonylsulfilimine compounds have the formula:

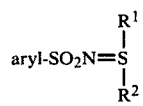

wherein $R^1$ and $R^2$ have the aforementioned definitions.

3. A method according to claim 1, wherein the alkali metal arylsulfochloramide is sodium benzenesulfochloramide or sodium toluenesulfochloramide.

4. A method according to claim 1, wherein the reaction is carried out in aqueous alcohol.

5. A method according to claim 1, wherein the mixture of arylsulfonylsulfilimine compounds in aqueous acetonitrile solution is separated by reverse phase high pressure liquid chromatography.

6. A method according to claim 2, wherein $R^1$ is 2-chlorethyl, 2-hydroxyethyl or vinyl, and $R^2$ is ethyl.

7. A method according to claim 2, wherein $R^1$ and $R^2$ are the same or different radicals from the group consisting of 2-chloroethyl, 2-hydroxyethyl amd vinyl.

8. A method according to claim 2, wherein the alkali metal arylsulfochloramide is sodium benzenesulfochloramide.

9. A method according to claim 8, wherein the reaction is carried out in aqueous alcohol.

10. A method according to claim 8, wherein the mixture of arylsulfonylsulfilimine compounds separated by HPCL is in aqueous acetonitrile solution.

* * * * *